(12) United States Patent
Takahashi et al.

(10) Patent No.: US 10,213,177 B2
(45) Date of Patent: Feb. 26, 2019

(54) X-RAY CT APPARATUS, DATA PROCESSING DEVICE, AND PROJECTION DATA GENERATION METHOD

(71) Applicant: HITACHI, LTD., Tokyo (JP)

(72) Inventors: Hisashi Takahashi, Tokyo (JP); Taiga Goto, Tokyo (JP); Koichi Hirokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 278 days.

(21) Appl. No.: 15/321,903

(22) PCT Filed: Jul. 23, 2015

(86) PCT No.: PCT/JP2015/070954
§ 371 (c)(1),
(2) Date: Dec. 23, 2016

(87) PCT Pub. No.: WO2016/021417
PCT Pub. Date: Feb. 11, 2016

(65) Prior Publication Data
US 2017/0135664 A1    May 18, 2017

(30) Foreign Application Priority Data
Aug. 4, 2014 (JP) .................. 2014-158472

(51) Int. Cl.
*A61B 6/00* (2006.01)
*A61B 6/03* (2006.01)
*A61B 6/04* (2006.01)

(52) U.S. Cl.
CPC ............ *A61B 6/5258* (2013.01); *A61B 6/032* (2013.01); *A61B 6/0407* (2013.01); *A61B 6/461* (2013.01)

(58) Field of Classification Search
CPC ..... A61B 6/5258; A61B 6/032; A61B 6/0407; A61B 6/461; G06T 11/005
See application file for complete search history.

(56) References Cited

U.S. PATENT DOCUMENTS

| | | | | |
|---|---|---|---|---|
| 4,654,796 A * | 3/1987 | Takagi | .................. | G06T 11/005 378/10 |
| 7,676,074 B2 * | 3/2010 | Sauer | .................... | G06T 11/005 382/128 |

FOREIGN PATENT DOCUMENTS

| | | |
|---|---|---|
| JP | 2004-065287 | 3/2004 |
| JP | 2008-113792 | 5/2008 |

OTHER PUBLICATIONS

LaRiviere et al. "Penalized-Likelihood Sinogram Restoration for Computed Tomography" IEEE Transactions on Medical Imaging, vol. 25, No. 8 (2006) (Year: 2006).*

(Continued)

*Primary Examiner* — Courtney D Thomas
(74) *Attorney, Agent, or Firm* — Cooper & Dunham LLP

(57) ABSTRACT

An X-ray CT apparatus includes an extraction unit that acquires air data measured using the X-ray CT apparatus and the measurement data obtained by scanning the object, that extracts sensitivity variation data which is a sensitivity variation component of a detection element from the air data, and that extracts blank data from which the sensitivity variation component is removed, and a projection data generation unit that removes the sensitivity variation component and noise which are included in the measurement data, based on the sensitivity variation data, and that uses the blank data so as to perform a correction process of the measurement data from which the sensitivity variation component and the noise are removed.

12 Claims, 11 Drawing Sheets

(56) References Cited

OTHER PUBLICATIONS

International Search Report in connection with PCT.JP2015/070954.

* cited by examiner

FIG.7
(a)
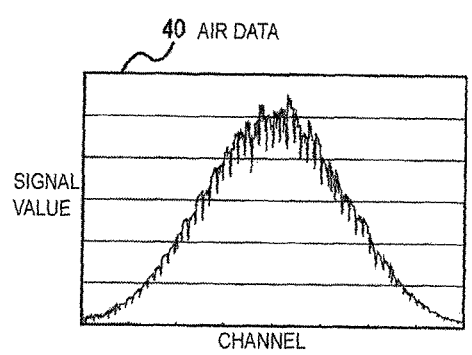
(b)
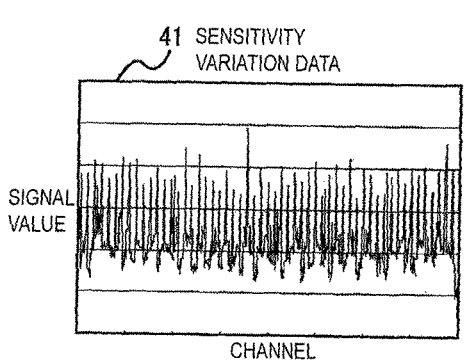
(c)
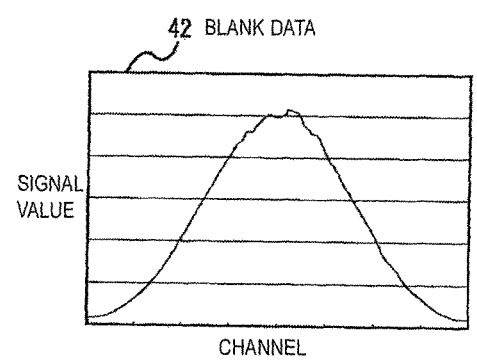

FIG.9
(a)
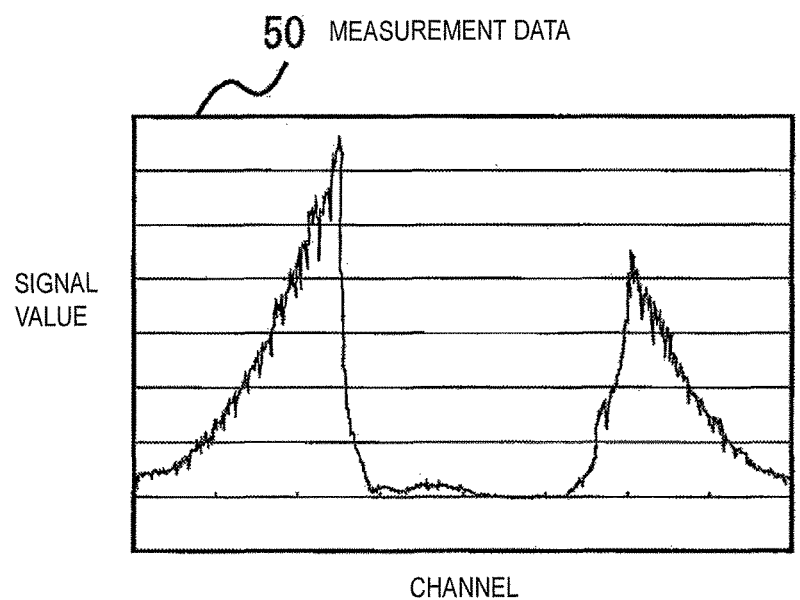
50 MEASUREMENT DATA
(b)
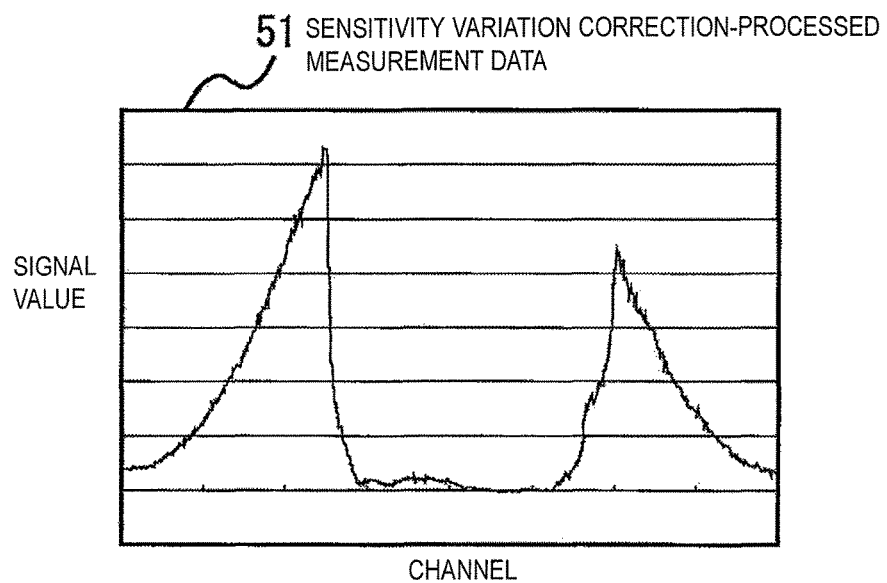
51 SENSITIVITY VARIATION CORRECTION-PROCESSED MEASUREMENT DATA

X-RAY CT APPARATUS, DATA PROCESSING DEVICE, AND PROJECTION DATA GENERATION METHOD

TECHNICAL FIELD

The present invention relates to an X-ray computed tomography (CT) apparatus, a data processing device, and a projection data generation method. In detail, the present invention relates to a noise reduction process of measurement data obtained by the X-ray CT apparatus.

BACKGROUND ART

The X-ray CT apparatus emits X-ray using multiple angles around an object, and causes an X-ray detector to acquire the X-ray attenuated by the object. An X-ray beam is shaped in such a way that the X-ray generated in an X-ray tube is transmitted through a bowtie filter, and thereafter, the X-ray beam is emitted to the object. In addition, the X-ray detector is configured so that multiple detector blocks having multiple X-ray detection elements are arrayed in parallel in a rotation direction (hereinafter, referred to as a channel direction) and a rotation axis direction (column direction) of the apparatus.

In a case where the X-ray detector having the multiple detector blocks is used in this way, a clearance is generated between the adjacent detector blocks. Due to this clearance, sensitivity variations occur between the detection element on an inner side of the detector blocks and the detection element on an, end side of the detector blocks. In another case, due to variations in a light receiving area which occur during a manufacturing process of the X-ray detector, the sensitivity variations occur between the respective detection elements. In particular, the sensitivity variations caused by the former factor always occur in a specific detection element, thereby causing a ring-like artifact to appear on an image. In order to restrain these sensitivity variations, the X-ray CT apparatus in the related art performs air correction on measurement data acquired by the X-ray detector.

According to the air correction in the related art, air data scanned in a state where the object is not present is measured in advance, and the air data is referred to as sensitivity of the detection element, thereby correcting a sensitivity variation component included in the measurement data scanned in a state where the object is present.

On the other hand, X-ray exposure affecting human bodies has become an issue in recent years. Accordingly, a technique has been actively studied in order to obtain image quality required for doctor's diagnosis even when scanning is performed by minimizing an X-ray exposure amount (even during low dose scanning). A representative method thereof includes a noise reduction method disclosed in PTL 1.

PTL 1 discloses a method of reducing noise included in measurement data by modelling statistical fluctuations of the measurement data which are caused by an X-ray detection process.

CITATION LIST

Patent Literature

PTL 1: U.S. Pat. No. 7,676,074

Non-Patent Literature

NPL 1: "Penalized-Likelihood Sinogram Restoration for Computed Tomography", P. J. La Riviere, J. Bian and P. A. Vargas, IEEE. Trans. Med. Imag., vol. 25, No. 8, 2006

SUMMARY OF INVENTION

Technical Problem

However, if the noise reduction process in the related art is applied to the measurement data, fluctuations in the measurement data which are caused by the sensitivity variations in the detection element are also regarded as the noise, thereby causing a possibility that the fluctuations may be reduced. Then, if the air correction is performed using the air data holding the sensitivity variations after the noise reduction process, there is a problem in that a ring-like artifact appears on an image.

On the other hand, in order to avoid the ring-like artifact from appearing on the image, it is conceivable to apply the noise reduction process to data subjected to the air correction by changing the above-described process procedure. However, in this case, X-ray attenuation in the bowtie filter is reflected in the air data. Thus, in view of the influence of the bowtie filter, noise reduction cannot be performed on the data subjected to the air correction. As a result, the noise is underestimated, thereby causing a problem in that a noise reduction effect is insufficiently achieved.

On the other hand, in a state where the bowtie filter is excluded, the sensitivity variations in the detection element can be separately scanned in advance. However, it becomes necessary to add an operation mechanism for excluding the bowtie filter to a usually used apparatus. Consequently, there is a problem of increased cost and complicated maintenance.

The present invention is made in view of the above-described problems, and an object thereof is to provide an X-ray CT apparatus, a data processing device, and a projection data generation method, which can generate projection data for obtaining an image with satisfactory image quality by accurately removing the influence of sensitivity variations in an X-ray detector which are included in measurement data obtained by the X-ray CT apparatus scanning an object.

Solution to Problem

In order to achieve the above-described object, an X-ray CT apparatus includes a scan gantry unit that emits X-ray to an object, and that detects the X-ray transmitted through the object, a bed on which the object is laid, and in which the object is loaded into or unloaded from an X-ray emission range of the scan gantry unit, and an operation desk including a data processing device that controls each portion of the scan gantry unit, that acquires measurement data measured by the scan gantry unit, and that generates an image including an object tomographic image from the measurement data. The data processing device includes an extraction unit that acquires air data measured using the X-ray CT apparatus and the measurement data obtained by scanning the object, that extracts sensitivity variation data which is a sensitivity variation component of a detection element from the air data, and that extracts blank data from which the sensitivity variation component is removed, and a projection data generation unit that removes the sensitivity variation component and noise which are included in the measurement data, based on the sensitivity variation data, and that uses the blank data so as to perform a correction process of the measurement data from which the sensitivity variation component and the noise are removed.

In addition, a data processing device acquires air data measured using an X-ray CT apparatus and measurement data obtained by scanning an object. The data processing device includes an extraction unit that that extracts sensitivity variation data which is a sensitivity variation component of a detection element from the air data, and that extracts blank data from which the sensitivity variation component is removed, and a projection data generation unit that removes the sensitivity variation component and noise which are included in the measurement data, based on the sensitivity variation data, and that uses the blank data so as to perform a correction process of the measurement data from which the sensitivity variation component and the noise are removed.

In addition, a projection data generation method includes a step of causing a data processing device to acquire air data measured using an X-ray CT apparatus and measurement data obtained by scanning an object, to extract sensitivity variation data which is a sensitivity variation component of a detection element from the air data, and to extract blank data from which the sensitivity variation component is removed, a step of removing the sensitivity variation component and noise which are included in the measurement data, based on the sensitivity variation data, and a step of performing a correction process using the blank data on the measurement data from which the sensitivity variation component and the noise are removed.

Advantageous Effects of Invention

According to the present invention, it is possible to provide an X-ray CT apparatus, a data processing device, and a projection data generation method, which can generate projection data for obtaining an image with satisfactory image quality by accurately removing the influence of sensitivity variations in an X-ray detector which are included in measurement data obtained by the X-ray CT apparatus scanning an object.

BRIEF DESCRIPTION OF DRAWINGS

FIG. 7(a) illustrates air data 40, FIG. 7(b) illustrates sensitivity variation data 41, and FIG. 7(c) illustrates blank data 42 obtained by performing an end element interpolation process and a smoothing process.

FIG. 9(a) illustrates measurement data 50, and FIG. 9(b) illustrates sensitivity variation correction-processed measurement data 51.

DESCRIPTION OF EMBODIMENTS

Hereinafter, embodiments according to the present invention will be described in detail with reference to the drawings.

First Embodiment

First, an X-ray CT apparatus 1 according to the present invention will be described.

Figure 1:
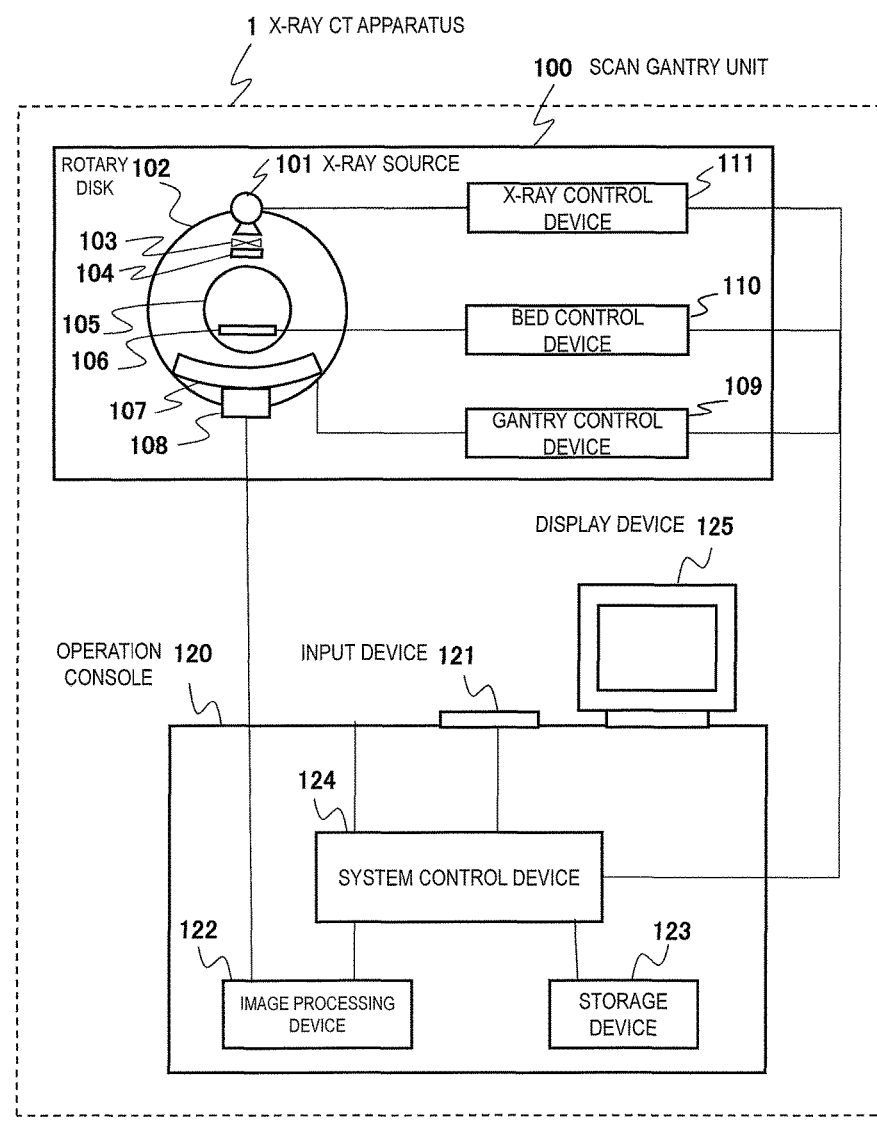
FIG. 1 is an overall configuration diagram of an X-ray CT apparatus 1.

FIG. 1 is an overall configuration diagram of the X-ray CT apparatus 1. As illustrated in FIG. 1, the X-ray CT apparatus 1 includes a scan gantry unit 100, a bed 106, and an operation desk 120. The scan gantry unit 100 is a device that emits X-ray to an object, and that detects the X-ray transmitted through the object. The operation desk 120 is a device that controls each portion of the scan gantry unit 100, that acquires transmitted X-ray data (measurement data) measured by the scan gantry unit 100, and that generates an image such as an object tomographic image from the measurement data. The bed 106 is a device on which the object is laid, and in which the object is loaded into or unloaded from an X-ray emission range of the scan gantry unit 100.

The scan gantry unit 100 includes an X-ray source 101, a rotary disc 102, a bowtie filter 103, a collimator 104, an X-ray detector 107, a data collection device 108, a gantry control device 109, a bed control device 110, and an X-ray control device 111.

The operation desk 120 includes an input device 121, a data processing device (image processing device) 122, a storage device 123, a system control device 124, and a display device 125.

An opening portion 105 is disposed in the rotary disc 102 of the scan gantry unit 100. The X-ray source 101 and the X-ray detector 107 are arranged to face each other via the opening portion 105. The object laid on the bed 106 is inserted into the opening portion 105. The rotary disc 102 is rotated around the object by a drive force transmitted through a drive transmission system from a rotary disc drive device. The rotary disc drive device is controlled by the gantry control device 109.

The X-ray source 101 is controlled by the X-ray control device 111, and continuously or intermittently emits X-ray having predetermined intensity. The X-ray control device 111 controls an X-ray tube voltage and an X-ray tube current to be applied or supplied to the X-ray source 101, in accordance with the X-ray tube voltage and the X-ray tube current which are determined by the system control device 124 of the operation desk 120.

The bowtie filter 103 and the collimator 104 are disposed in an X-ray emission port of the X-ray source 101. The bowtie filter 103 is a device for adjusting the X-ray emitted from the X-ray source 101 so as to be incident on the X-ray detector 107 with uniform intensity. The collimator 104 is a device for limiting an emission range of the X-ray which is emitted from an X-ray tube 101 and which is adjusted by the bowtie filter 103. For example, the collimator 104 is shaped in a cone beam (conical or pyramidal beam). An opening width of the collimator 104 is controlled by the system control device 124.

The X-ray which is emitted from the X-ray source 101, which passes through the bowtie filter 103 and the collimator 104, and which is transmitted through the object is absorbed (attenuated) in each tissue inside the object, passes through the object, and is incident on the X-ray detector 107.

For example, in the X-ray detector 107, an X-ray detection element group configured to have a combination of a scintillator and a photodiode is two-dimensionally arrayed in a channel direction (circumferential direction) and a column direction (body axis direction). A structure of the X-ray detector 107 will be described later (refer to FIGS. 2 and 3).

The X-ray detector 107 is disposed so as to face the X-ray source 101 via the object. The X-ray detector 107 detects the amount of the X-ray transmitted through the object, and outputs the amount of the X-ray to the data collection device 108.

The data collection device 108 collects the amount of the X-ray detected by each X-ray detection element of the X-ray detector 107 at a predetermined sampling interval, and converts the amount of the X-ray into a digital signal. As the measurement data, the data collection device 108 sequentially outputs the digital signal to the image processing device 122 of the operation desk 120. In order to correct the sensitivity of the X-ray detector 107 and the like, the data collection device 108 uses air data. The air data is the measurement data scanned in a state where the object is not present.

The image processing device 122 acquires the measurement data input from the data collection device 108, and performs a predetermined preprocessing on the measurement data, thereby generating projection data required for reconfiguration. The image processing device 122 uses the generated projection data so as to reconfigure an object image such as a tomographic image. The system control device 124 causes the storage device 123 to store object image data reconfigured by the image processing device 122, and causes the display device 125 to display the object image data. The image processing device 122 may cause the storage device 123 to store the measurement data input from the data collection device 108. The image processing device 122 may perform a projection data generation process after reading the measurement data at any optional timing different from scanning timing.

In the projection data generation process performed by the image processing device 122, output offset correction is generally performed using a dark current of the X-ray detector 107. Thereafter, for example, a noise reduction process is performed using an inter-proximity element smoothing process or the like. An air correction process is performed using the air data on noise-reduced data. Thereafter, a reference correction process, a logarithm transformation process, and a phantom correction process for restraining a beam hardening effect, and the like are performed by using a value of a reference detector, thereby generating the projection data.

However, in the projection data generated in the above-described procedure, a ring-like artifact or the like appears due to sensitivity variations in the detection element. Therefore, the image processing device 122 according to the present invention extracts the sensitivity variations between the detection elements which are included in the air data, as sensitivity variation data. The image processing device 122 extracts and stores blank data obtained by removing a sensitivity variation component from the air data.

Then, after removing the sensitivity variation component included in the object measurement data, based on the above-described sensitivity variation data, the image processing device 122 performs the noise reduction process. Thereafter, the image processing device 122 performs a correction process using the above-described blank data on the measurement data from which the sensitivity variation component and the noise are removed. Thereafter, similarly to the projection data generation process in the related art, the reference correction process, the logarithm transformation process, and the phantom correction process and the like are performed so as to generate the projection data. A process of separating and extracting the sensitivity variation data and the blank data from the air data, and the projection data generation process will be described in detail later.

The system control device 124 is a computer including a central processing unit (CPU), a read only memory (ROM), and random access memory (RAM) and the like. The storage device 123 is a data recording device such as a hard disk, and stores in advance a program or data or the like for realizing a function of the X-ray CT apparatus 1.

The display device 125 is configured to include a display device such as a liquid crystal panel and a CRT monitor, and a logic circuit for performing a display process in cooperation with the display device, and is connected to the system control device 124. The display device 125 displays the object image output from the image processing device 122, and various information items handled by the system control device 124.

For example, the input device 121 is configured to include a keyboard, a pointing device such as a mouse, ten keys, and various switch buttons and the like, and outputs various instructions or information items input by an operator to the system control device 124. The operator interactively operates the X-ray CT apparatus 1 by using the display device 125 and the input device 121. The input device 121 may be a touch panel-type input device configured to be integral with a display screen of the display device 125.

The bed 106 includes a top plate on which the object is laid, a vertical moving device, and a top plate drive device. A height of the top plate is vertically raised and lowered under the control of the bed control device 110. The top plate is longitudinally moved in a body axis direction, or laterally moved in a direction perpendicular to the body axis and in a direction parallel to a floor surface (in the rightward and leftward direction in the drawing). During scanning, the bed control device 110 moves the top plate at a bed moving speed and in a bed moving direction which are determined by the system control device 124.

Figure 2:
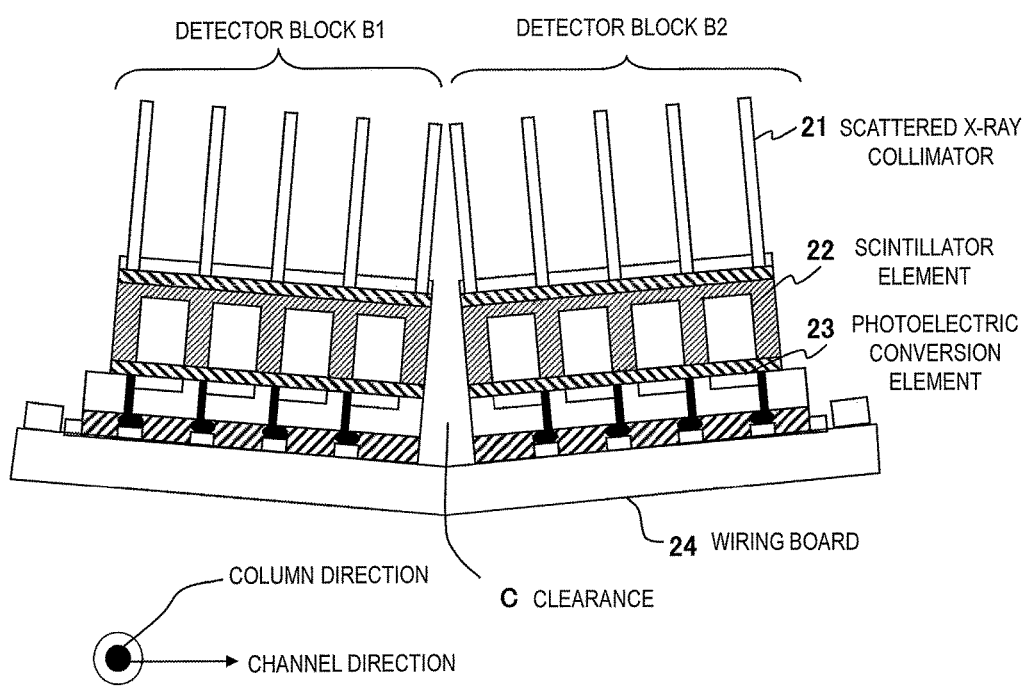
FIG. 2 is a layout view when adjacent detector blocks B1 and B2 are viewed in a column direction.
Figure 3:
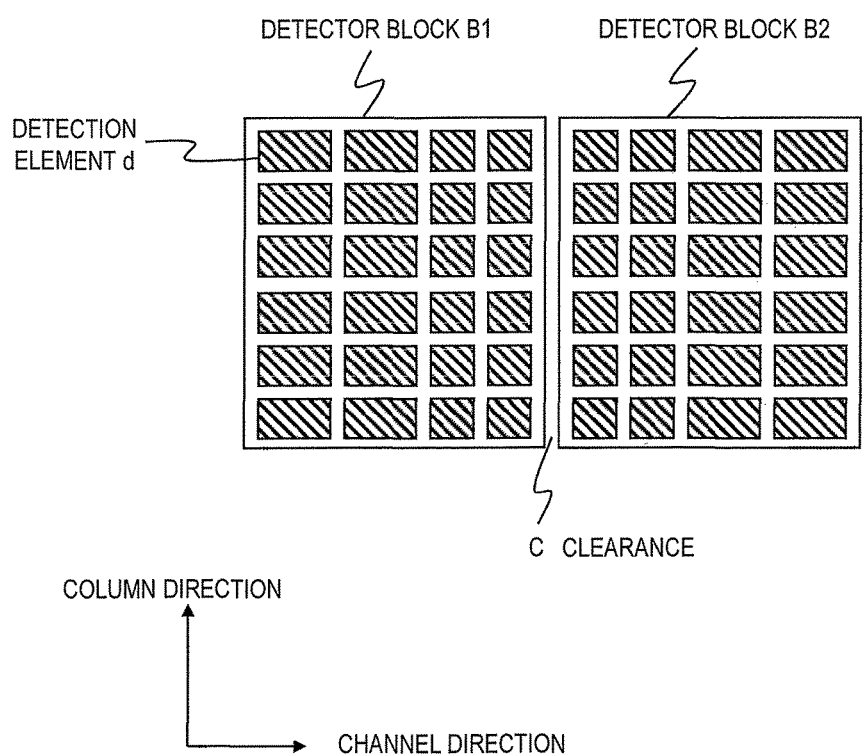
FIG. 3 is a view when the adjacent detector blocks B1 and B2 are viewed in an X-ray emission direction.

Next, a structure of the X-ray detector 107 will be described with reference to FIGS. 2 and 3. FIG. 2 is a view when an arrangement of two adjacent detector blocks B1 and B2 in the X-ray detector 107 are viewed in the column direction. FIG. 3 is a view when viewed in the X-ray emission direction.

As illustrated in FIGS. 2 and 3, the respective detector blocks B1 and B2 are configured so that multiple detection elements d having a scintillator element 22 and a photoelectric conversion element 23 are arrayed in the channel direction and the column direction. In addition, scattered X-ray collimators 21 are disposed parallel to each other in the channel direction and the column direction so that the X-ray scattered in the object is less likely to be incident on the detection elements d. The detector blocks B1 and B2 are arranged on an arc along the rotary disc 102. Therefore, as illustrated in FIGS. 2 and 3, a clearance C is generated between the adjacent detector blocks B1 and B2. Due to the clearance C, sensitivity variations occur in an end element and an internal element of the respective detector blocks B1 and B2 in the X-ray detector 107. These cause the ring-like artifact on the image.

Figure 4:
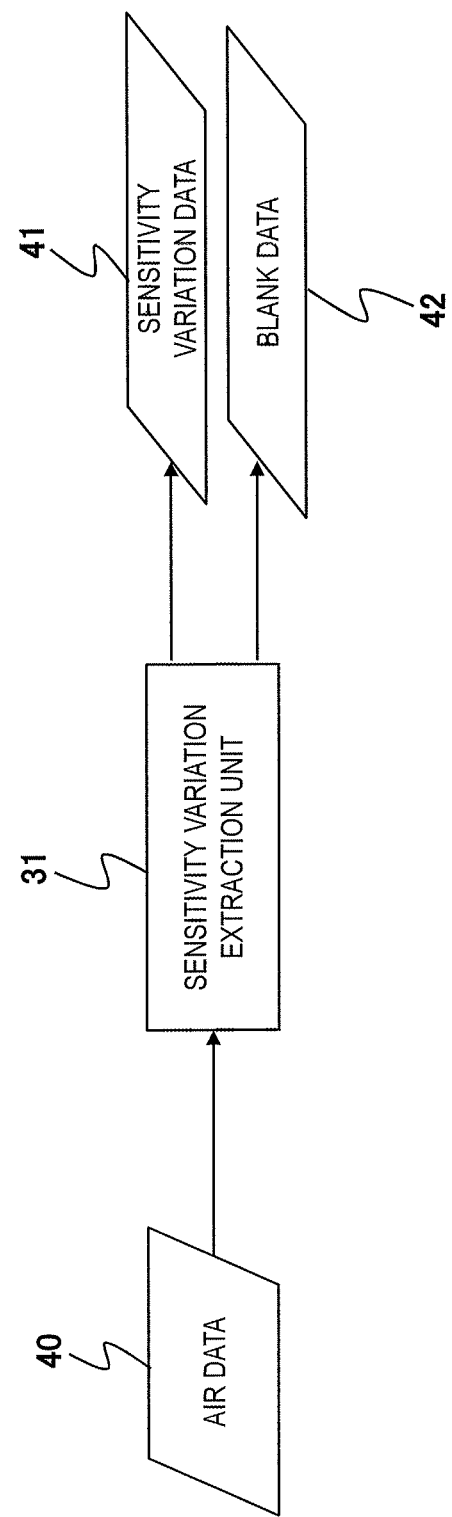
FIG. 4 is a view illustrating a function of a sensitivity variation extraction unit 31.
Figure 5:
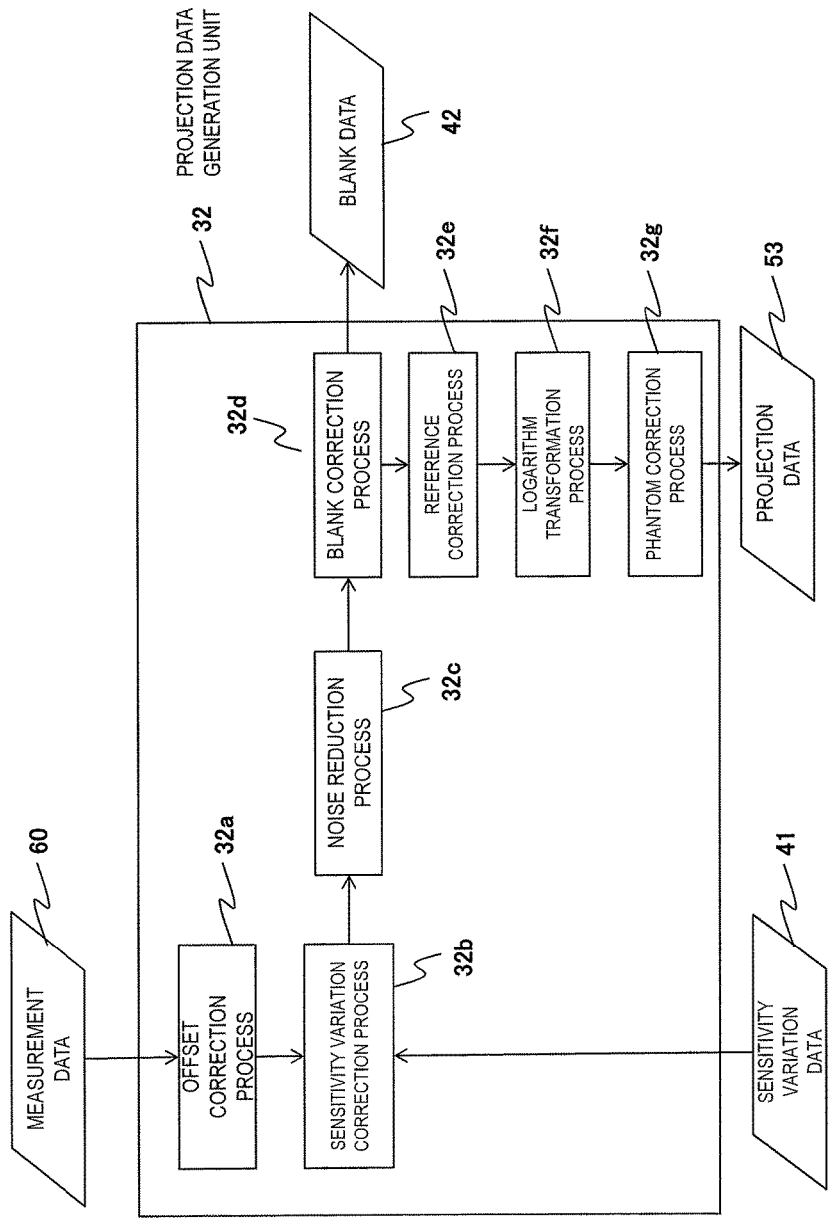
FIG. 5 is a view illustrating a function of a projection data generation unit 32.

Therefore, as illustrated in FIGS. 4 and 5, the image processing device 122 of the X-ray CT apparatus 1 according to the present invention includes a sensitivity variation extraction unit 31 and a projection data generation unit 32. Referring to FIGS. 4 and 5, the sensitivity variation extraction unit 31 and the projection data generation unit 32 in the image processing device 122 according to the present invention will be described.

As illustrated in FIG. 4, the sensitivity variation extraction unit 31 acquires air data 40 which is the measurement data obtained by scanning in a state where the object is not present, and extracts a sensitivity variation component between the detection elements of the X-ray detector 107 which is included in the air data 40, as sensitivity variation data 41. The sensitivity variation extraction unit 31 removes the sensitivity variation component from the air data 40, and extracts blank data 42. The sensitivity variation data 41 and the blank data 42 which are extracted are stored in the storage device 123 (refer to FIG. 7).

According to the invention described below, the air data 40 is data prior to the logarithm transformation, in which an offset correction process and a reference correction process are applied to the measurement data obtained in a state where the object is not present. It is desirable to periodically scan the air data 40. In addition, the air data 40 is scanned under each scanning condition such as a scanner's rotation speed and a collimator's opening width, and each air data 40 is stored in the storage device 123.

As illustrated in FIG. 5, the projection data generation unit 32 acquires measurement data 50 obtained by scanning the object, and performs an offset correction process 32a. Thereafter, referring to the above-described sensitivity variation data 41, the projection data generation unit 32 performs a sensitivity variation correction process 32b. Subsequently, the projection data generation unit 32 applies a noise reduction process 32c to the measurement data 51 (refer to FIG. 9) from which the sensitivity variation component is removed by performing the sensitivity variation correction process 32b. Furthermore, a blank correction process 32d is performed using the above-described blank data 42 on the measurement data from which the sensitivity variation component and the noise are removed. In this manner, it is possible to acquire object attenuation data from which the influence of the X-ray attenuation is removed by the bowtie filter 103 and which indicates the X-ray attenuation of only the object. The projection data generation unit 32 applies a reference correction process 32e, a logarithm transformation process 32f, and a phantom correction process 32g to the object attenuation data, thereby preparing projection data 53 required for obtaining a tomographic image. The sensitivity variation correction process 32b, the noise reduction process 32c, and the blank correction process 32d will be described later.

Figure 8:
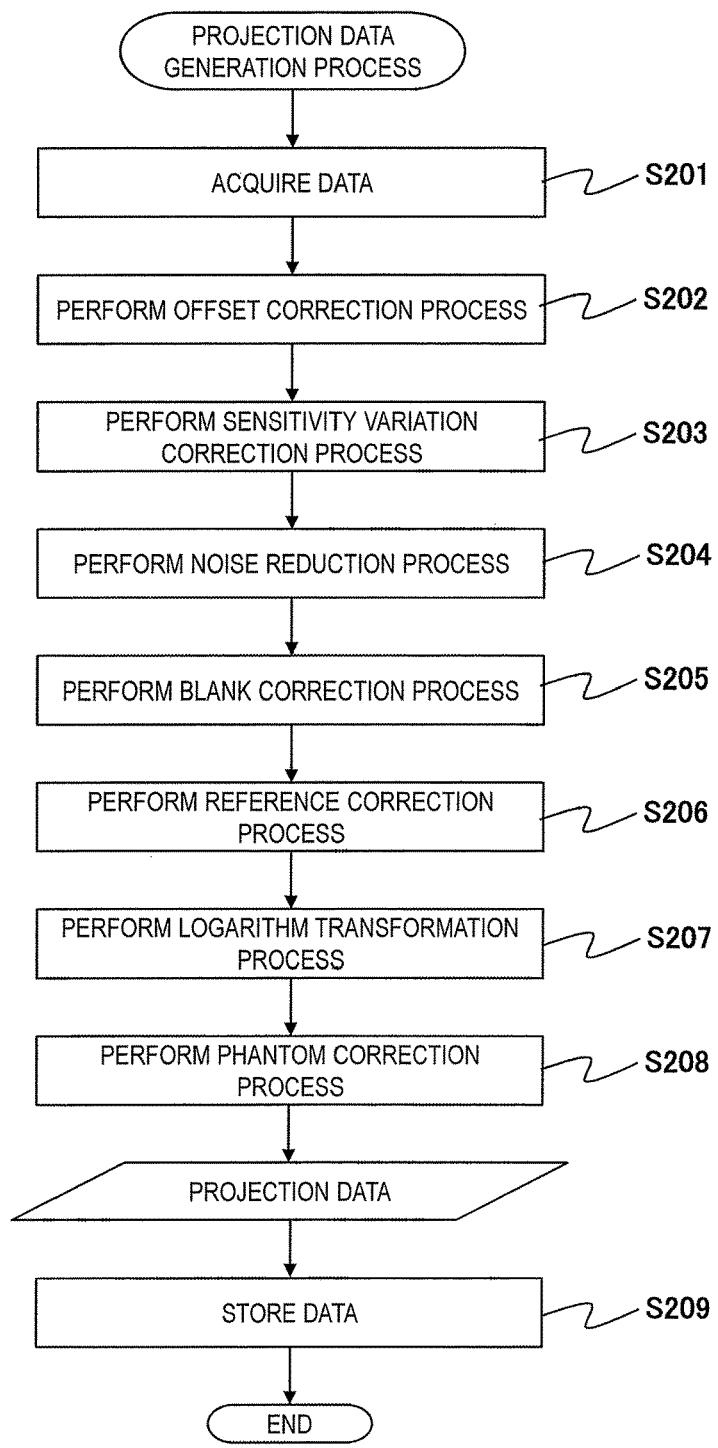
FIG. 8 is a flowchart illustrating a procedure in a projection data generation process.

Next, referring to FIGS. 6 to 8, an operation of the X-ray CT apparatus 1 will be described.

Figure 6:
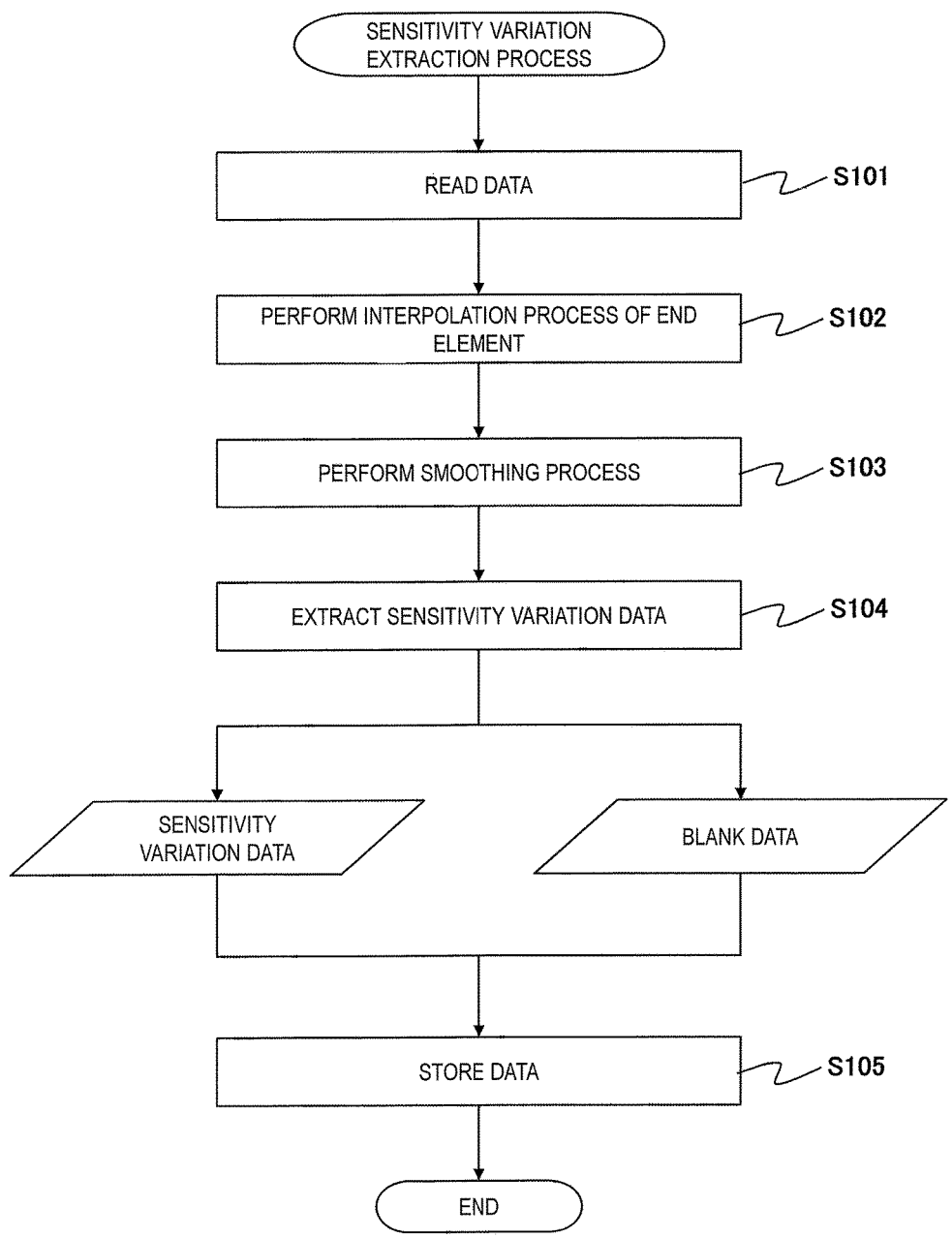
FIG. 6 is a flowchart illustrating a procedure in a sensitivity variation extraction process.

The image processing device 122 of the X-ray CT apparatus performs a sensitivity variation extraction process in accordance with a procedure illustrated in a flowchart in FIG. 6. In addition, the image processing device 122 uses the sensitivity variation data 41 and the blank data 42 which are extracted by the sensitivity variation extraction process so as to perform the projection data generation process illustrated in FIG. 8.

Prior to the sensitivity variation extraction process, the air data 40 is scanned under various scanning conditions, and is stored in the storage device 123. In addition, an end element map is prepared in advance, and is stored in the storage device 123.

The end element map is prepared by mapping positions (numbers in the channel direction and the column direction) of the detection elements located in end portions of the respective detector blocks B1, B2, . . . of the X-ray detector 107. For example, in a detector block B having a detection element of I-th channel and J-th column, numbers of i{1, . . . , i, . . . , I} and j{1, . . . , j, . . . , I} are respectively given in the channel direction and the column direction of the detection element. Furthermore, a value of the end element map of the detection element of i-th channel and j-th column is set to $b_{i,j}$. The value is held as $b_{i,j}=0$ in a case of the element located in the end portion and $b_{i,j}=1$ in a case of the element located in the inner portion. The element located in the end portion is determined in advance in accordance with a clearance size and a channel width of the detector block. In addition, in a case where the number of the detector blocks configuring the X-ray detector 107 and the number of the detection elements inside the detector block are changed, information of the end element map can be changed in accordance with these changes.

In the sensitivity variation extraction process illustrated in FIG. 6, the image processing device 122 first performs a data reading process (Step S101). In Step S101, the image processing device 122 reads the air data 40 and the end element map corresponding to the scanning condition from the storage device 123. In the following description, a value of the air data 40 in the detection element of i-th channel and j-th column is expressed by $p_{i,j}$.

Referring to the air data 40 and the end element map which are read in Step S101, the image processing device 122 performs interpolation and extrapolation on the end element of the detector block (Step S102). In the following description, a method of independently performing the interpolation in the channel direction and the column direction will be described. However, it is also possible to simultaneously performing the interpolation on two dimensions in the channel direction and the column direction.

In Step S102, the image processing device 122 first performs the interpolation in the channel direction, except for the detection element belonging to a column of $b_{i,j}=0$ (∀j). Lagrange interpolation is performed on the $N_s$ to $N_e$ number of neighbor data items for i-th channel, thereby calculating interpolation data $p'_{i,j}\_ch$ in the channel direction of the detection element of $b_{i,j}0$ as expressed in Expression (1) below.

[Expression 1]

$$p'_{i,j}\_ch = \sum_{k=N_s}^{N_e} a_k(i,j) p_{k,j} b_{k,j} \quad (1)$$

Here, a correction coefficient $a_k(i, j)$ is expressed by Expression (2) below.

[Expression 2]

$$a_k(i,j) = \prod_{\substack{t=N_s, t \neq k, \\ b_{i,j} \neq 0}}^{N_e} \frac{i-t}{k-t} \quad (2)$$

The interpolation data $p'_{i,j}\_ch$ in the channel direction obtained by Expression (1) and Expression (2) above and the original air data 40 are combined with each other, thereby calculating interpolation-purpose data p'$_{i,\_j}$_sl in the column direction as expressed in Expression (3) below.

[Expression 3]

$$p'_{i,j\_sl} = \begin{cases} P_{i,j} & \text{if } b_{i,j} = 1 \\ p'_{i,j\_ch} & \text{else} \end{cases} \forall i, j \quad (3)$$

Furthermore, in Expression (3), $b_{i,j}=1$ is substituted in the detection element of p'$_{i,\_j}$_ch=p'$_{i,\_j}$_sl. Then, with regard to the detection element belonging to the column of the $b_{i,j}=0$ ($\forall$j), the Lagrange interpolation is performed on the $M_s$ to $M_e$ number of neighbor data items for j-th column, thereby calculating interpolation data p"$_{i,j}$ of the detection element of $b_{i,j}=0$ as expressed in Expression (4) below.

[Expression 4]

$$p''_{i,j} = \sum_{k=M_s}^{M_e} a'_k(i,j) \cdot p'_{k,j\_sl} \cdot b_{k,j} \quad (4)$$

Here, an interpolation coefficient a'$_k$(i, j) is expressed by Expression (5) below.

[Expression 5]

$$a'_k(i,j) = \prod_{\substack{t=M_s, t \neq k, \\ b_{i,j} \neq 0}}^{M_e} \frac{j-t}{k-t} \quad (5)$$

The interpolation data obtained by Expression (4) and Expression (5) and the interpolation-purpose data in the column direction are combined with each other, thereby calculating interpolated data p'''$_{i,j}$ as expressed in Expression (6) below.

[Expression 6]

$$p'''_{i,j} = \begin{cases} p'_{i,j\_sl} & \text{if } b_{i,j} = 1 \\ p''_{i,j} & \text{else} \end{cases} \forall i, j \quad (6)$$

According to the above-described process, the interpolated data can be obtained in which the sensitivity variations are corrected between the detection elements of the inner portion and the end portion of the detector block. Here, an example using the Lagrange interpolation has been described. However, for example, a known interpolation method such as spline interpolation may be used.

Next, a Gaussian filter is applied in the channel direction and the column direction of the interpolated data (smoothing process; Step S103) so as to obtain the blank data 42. According to the process in Step S103, the sensitivity variations between the detection elements which occur due to a size of a light receiving area generated mainly in a detector manufacturing process are corrected.

FIG. 7(a) is a view of the air data 40 read in Step S101. FIG. 7(c) is a view illustrating an example of the blank data 42 obtained by the end element interpolation process and the smoothing process in Step S102 and Step S103. The blank data 42 is data from which the sensitivity variation component is removed and which reflects only the X-ray attenuation obtained using the bowtie filter 103.

In the smoothing process in Step S103, without being limited to the Gaussian filter, a known smoothing filter such as a movement averaging filter may be used.

Next, the image processing device 122 obtains a difference between the air data 40 and the blank data 42 in each detection element, and extracts the sensitivity variation data 41 (Step S104). FIG. 7(b) is an example of the sensitivity variation data 41 obtained by the process in Step S104. As illustrated in FIG. 7 (b), the sensitivity variation data 41 is data obtained by extracting only the sensitivity variation component removed from the air data 40 by the process in Step S102 and Step S103.

The image processing device 122 causes the storage device 123 to store the sensitivity variation data 41 and the blank data 42 (Step S105), and completes the sensitivity variation extraction process.

The above-described sensitivity variation extraction process may be performed at any timing as long as the process is performed from when the object starts to be scanned until the sensitivity variation correction process (Step S203) is performed in the projection data generation process to be described later (refer to FIG. 8). Alternatively, the sensitivity variation extraction process may be performed immediately after the air data is scanned, and the data may be stored in the storage device 123.

Next, referring to FIG. 8, the projection data generation process will be described.

First, the image processing device 122 acquires the measurement data 50 obtained by scanning the object under a predetermined scanning condition, from the data collection device 108 or the storage device 123 (Step S201). If the measurement data 50 is acquired, the image processing device 122 applies the offset correction process to the acquired measurement data 50 (Step S202). Thereafter, the image processing device 122 performs the sensitivity variation correction process (Step S203).

In the sensitivity variation correction process in Step S203, the image processing device 122 acquires the sensitivity variation data 41 from the storage device 123, and divides the measurement data 50 by the sensitivity variation data 41. In this manner, the image processing device 122 calculates sensitivity variation correction-processed measurement data 51. In this case, the same sensitivity variation data 41 in a viewing direction is applied to the measurement data 50 of the detection element in any optional channel and column.

FIG. 9(a) illustrates an example of the offset correction-processed measurement data 50 in Step S202. FIG. 9(b) illustrates an example of the sensitivity variation correction-processed measurement data 51 in Step S203.

Similarly to the related art, the image processing device 122 applies the noise reduction process to the sensitivity variation correction-processed measurement data 51 as illustrated in FIG. 9(b) (Step S204). For example, in the noise reduction process, an inter-proximity element smoothing process may be performed. Thereafter, the image processing device 122 applies the blank correction process to noise reduction-processed measurement data (Step S205).

In the blank correction process in Step S205, the image processing device 122 acquires the blank data 42 from the storage device 123, and divides the noise reduction-processed measurement data (processed data in Step S204) by the blank data 42. In this manner, it is possible to obtain X-ray attenuation data of only the object (hereinafter, referred to as object attenuation data) which has no attenuation using the bowtie filter 103.

Thereafter, the image processing device 122 applies the reference correction (Step S206), the logarithm transformation process (Step S207), and the phantom correction process (Step S208) in the related art to the above-described object attenuation data, and obtains the projection data 53. The image processing device 122 causes the storage device 123 to store the generated projection data 53 (Step S209), and completes a series of the projection data generation processes.

As described above, the X-ray CT apparatus 1 includes the scan gantry unit 100 that emits the X-ray to the object, and that detects the X-ray transmitted through the object, the bed 106 on which the object is laid, and in which the object is loaded into or unloaded from the X-ray emission range of the scan gantry unit 100, and the operation desk 120 including the image processing device 122 that controls each portion of the scan gantry unit 100, that acquires the measurement data measured by the scan gantry unit 100, and that generates the image including the object tomographic image from the measurement data. The image processing device 122 includes the extraction unit 31 that acquires the air data measured using the X-ray CT apparatus 1 and the measurement data obtained by scanning the object, that extracts the sensitivity variation data which is the sensitivity variation component of the detection element from the air data, and that extracts the blank data from which the sensitivity variation component is removed, and the projection data generation unit 32 that removes the sensitivity variation component and the noise which are included in the measurement data, based on the sensitivity variation data, and that uses the blank data so as to perform the correction process of the measurement data from which the sensitivity variation component and the noise are removed.

In addition, the image processing device 122 includes the sensitivity variation extraction unit 31 that acquires the air data 40 measured using the X-ray CT apparatus 1 and the measurement data obtained by scanning the object, that extracts the sensitivity variation data 41 which is the sensitivity variation component of the detection element from the air data 40, and that extracts the blank data 40 from which the sensitivity variation component is removed, and the projection data generation unit 32 that removes the sensitivity variation component and the noise which are included in the measurement data, based on the sensitivity variation data 41, and that uses the blank data 40 so as to perform the correction process of the measurement data from which the sensitivity variation component and the noise are removed.

In addition, the projection data generation method includes the step of causing the data processing device to acquire the air data measured using the X-ray CT apparatus and the measurement data obtained by scanning the object, to extract the sensitivity variation data which is the sensitivity variation component of the detection element from the air data, and to extract the blank data from which the sensitivity variation component is removed, the step of removing the sensitivity variation component and the noise which are included in the measurement data, based on the sensitivity variation data, and the step of performing the correction process using the blank data on the measurement data from which the sensitivity variation component and the noise are removed.

That is, as the sensitivity variation data 41, the image processing device 122 extracts the sensitivity variation component between the detection elements which are included in the air data 40 obtained by scanning of the X-ray CT apparatus 1, and extracts the blank data 42 from which the sensitivity variation component is removed, from the air data 40. Then, after removing the sensitivity variation component included in the measurement data 50 obtained by scanning the object, based on the above-described sensitivity variation data 41, the image processing device 122 performs the noise removal process (for example, the inter-proximity element smoothing process).

Thereafter, the correction process using the blank data 42 is performed on the measurement data 50 from which the sensitivity variation component and the noise are removed. In this manner, the object attenuation data from which the influence of the X-ray attenuation is removed by the bowtie filter 103 and which indicates the X-ray attenuation of only the object is extracted. The reference correction process, the logarithm transformation process, and the phantom correction process and the like are performed on the object attenuation data, thereby preparing the projection data 53 required for preparing the object tomographic image.

If an image is reconfigured using this projection data 53, it is possible to prepare an image having no influence of the sensitivity variations in the detection element. Accordingly, it is possible to restrain a ring-like artifact from appearing on the image. In addition, the blank correction process is performed after the noise reduction process. Accordingly, it is possible to consider the X-ray attenuation in the bowtie filter 103, and it is possible to perform a proper noise reduction process.

In the description above, the sensitivity variation correction or the blank correction is performed on the measurement data before the logarithm transformation. However, without being limited thereto, the sensitivity variation correction or the blank correction may be performed after the logarithm transformation. That is, the measurement data after the logarithm transformation is subtracted from the sensitivity variation data obtained from the air data after the logarithm transformation. In this manner, it is possible to obtain the measurement data after the sensitivity variation correction.

In addition, after removing the sensitivity variation component included in the measurement data, based on the sensitivity variation data, the projection data generation unit may perform the inter-proximity element smoothing process for removing the noise, and may perform the correction process.

In addition, in the step of performing the correction process, after the sensitivity variation component included in the measurement data is removed, based on the sensitivity variation data, the inter-proximity element smoothing process for removing the noise may be performed.

Second Embodiment

Next, a second embodiment according to the present invention will be described.

A configuration of the X-ray CT apparatus 1 according to the second embodiment is the same as that according to the first embodiment. Hereinafter, repeated description will be omitted, and description will be made by giving the same reference numerals to each unit which is the same as that according to the first embodiment.

According to the first embodiment, the noise reduction process is performed on the data 51 obtained by removing the sensitivity variation component from the offset correction-processed measurement data. However, if an evaluation function established by using the sensitivity variation data 41 in the noise reduction process is used, a sensitivity variation component removal process can be included in the noise reduction process. That is, according to the second embodiment, a successive approximation noise reduction method included in the evaluation function established by using the sensitivity variation data 41 extracted from the air data 40 is employed. In this manner, it is possible to simultaneously perform the removal of the sensitivity variation component and the removal of the noise from the offset correction-processed measurement data 50.

Figure 10:
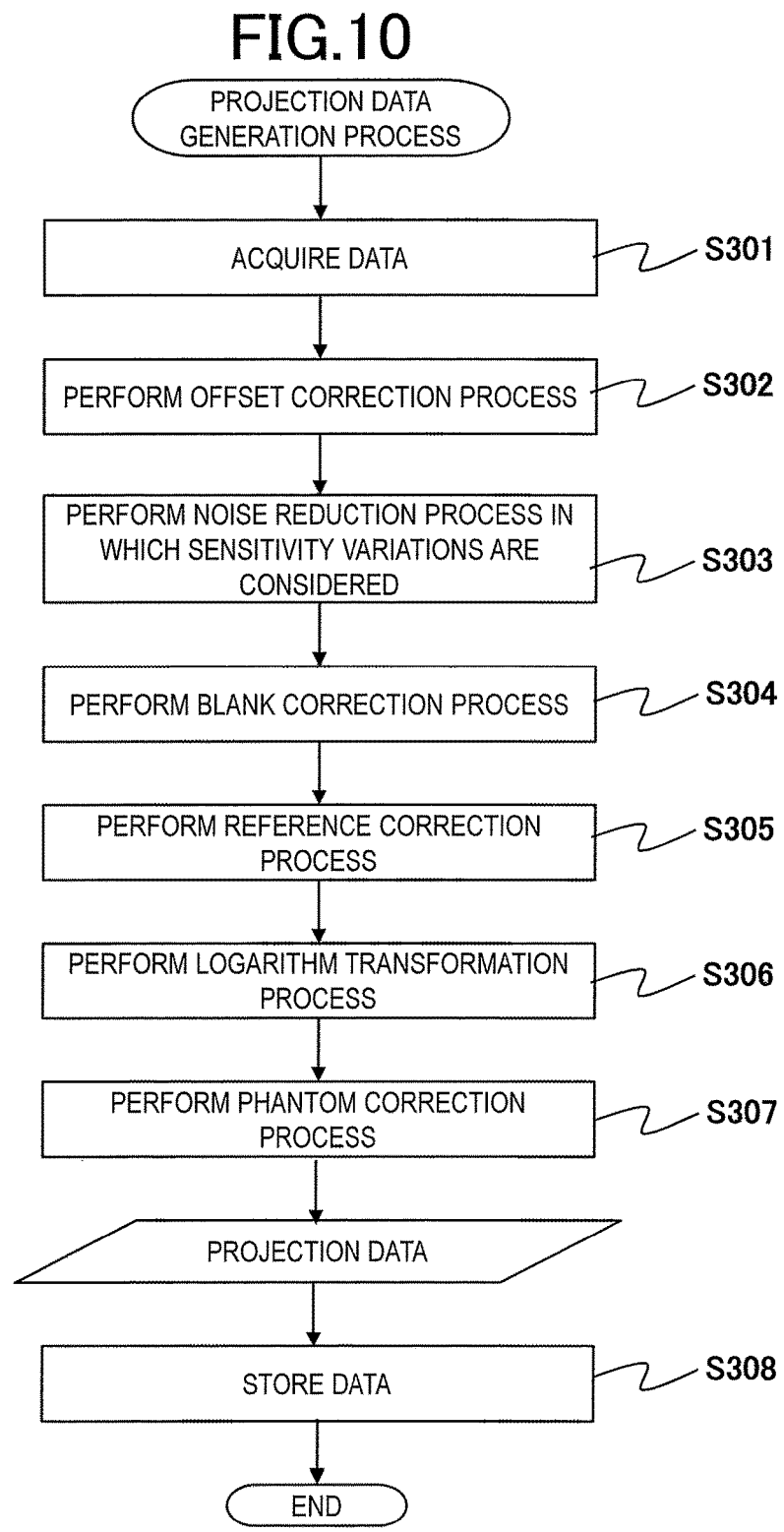
FIG. 10 is a flowchart illustrating a procedure in a projection data generation process according to a second embodiment.

FIG. 10 is a flowchart illustrating a procedure in a projection data generation process according to the second embodiment.

The sensitivity variation data 41 and the blank data 42 which are used in the projection data generation process are separated and extracted from the air data 40 in the same procedure (refer to FIG. 6) as that according to the first embodiment, and are stored in the storage device 123.

Hereinafter, the procedure in the projection data generation process according to the second embodiment will be described.

First, the image processing device 122 acquires the measurement data 50 obtained by scanning the object under a predetermined scanning condition, from the data collection device 108 or the storage device 123 (Step S301). If the measurement data 50 is acquired, the image processing device 122 applies the offset correction process (Step S302). Thereafter, the image processing device 122 performs the noise reduction process in which the sensitivity variations are considered (Step S303).

The noise reduction process in which the sensitivity variations are considered in Step S303 will be described.

The image processing device 122 acquires the offset correction-processed measurement data and the sensitivity variation data 41. Hereinafter, the offset processed-measurement data of i-th channel and j-th column is expressed as $y_{i,j}$. In addition, noise-reduced measurement data targeted for estimation is expressed as $x_{i,j}$.

In general, in a system in which the average $x_{i,j}$ number of X-ray photons is measured for the X-ray corresponding to a single color, a probability of detecting the $y_{i,j}$ number of X-ray photons can be modeled using Poisson distribution. The simultaneous probability of all detection elements of the X-ray detector 107 is expressed by Expression (7) below.

[Expression 7]

$$P(y_{1,1}, y_{1,2}, \ldots, y_{I,J} | x_{1,1}, x_{1,2}, \ldots, x_{I,J}) = \prod_{i=1}^{I} \prod_{j=1}^{J} \frac{x_{i,j}^{y_{i,j}} e^{-x_{i,j}}}{y_{i,j}!} \quad (7)$$

Expression (7) is called a likelihood function, and $y_{i,j}$ which maximizes the likelihood function is obtained by using a successive approximation method. In this manner, statistical noise can be effectively reduced. In addition, NPL 1 discloses a method of maximizing a posterior probability obtained in such a way that the likelihood function is multiplied by a prior probability. However, according to the method in the related art disclosed in NPL 1, the sensitivity variations in the detection element are not considered.

According to the second embodiment, the sensitivity variation data 41 of i-th channel and j-th column is set to $z_{i,j}$, and the noise-reduced measurement data in a state having no sensitivity variation is set to $x'_{i,j}$.

Then, the likelihood function of Expression (7) above is substituted with Expression (8) below.

[Expression 8]

$$P(y_{1,1}, y_{1,2}, \ldots, y_{I,J} | x'_{1,1}, x'_{1,2}, \ldots, x'_{I,J}) = \prod_{i=1}^{I} \prod_{j=1}^{J} \frac{z_{i,j} x'^{y_{i,j}}_{i,j} e^{-z_{i,j} x'_{i,j}}}{y_{i,j}!} \quad (8)$$

In the noise process in Step S303, Expression (8) is for optimization similarly to NPL1, for example. The sensitivity variation and noise-reduced data $x'_{i,j}$ is successively and approximately estimated.

According to the process in Step S303, the blank correction process is performed using the blank data 42 on the sensitivity variation component and noise-reduced measurement data (Step S304).

In the blank correction process, similarly to the first embodiment, the image processing device 122 divides the sensitivity variation component and noise reduction-processed measurement data by the blank data 42, thereby obtaining the object attenuation data.

Thereafter, similarly to Step S206 to Step S209 in FIG. 7, the image processing device 122 applies the reference correction process (Step S305), the logarithm transformation process (Step S306), and the phantom correction process (Step S307) in the related art, to the object attenuation data obtained in the process until Step S304, thereby obtaining the projection data 53. The image processing device 122 causes the storage device 123 to store the generated projection data 53 (Step S308), and completes a series of the projection data generation processes.

As described above, the projection data generation unit 32 removes the sensitivity variation component and the noise from the measurement data by employing the successive approximation noise reduction method using the evaluation function including the sensitivity variation data, and perform the correction process.

In addition, in the step of performing the correction process, the sensitivity variation component and the noise are removed from the measurement data by employing the successive approximation noise reduction method using the evaluation function including the sensitivity variation data.

In this way, according to the process in the second embodiment, the process of removing the sensitivity variation component can be included in the noise reduction process. If this process procedure is employed, even in a case where the sensitivity variation data cannot be accurately extracted from the air data, the noise reduction process can be more accurately performed, compared to the process procedure according to the first embodiment.

Third Embodiment

Next, a third embodiment according to the present invention will be described.

According to the third embodiment, operator's selection is received with regard to whether or not the noise reduction process considering the sensitivity variations is to be performed on the measurement data.

Figure 11:
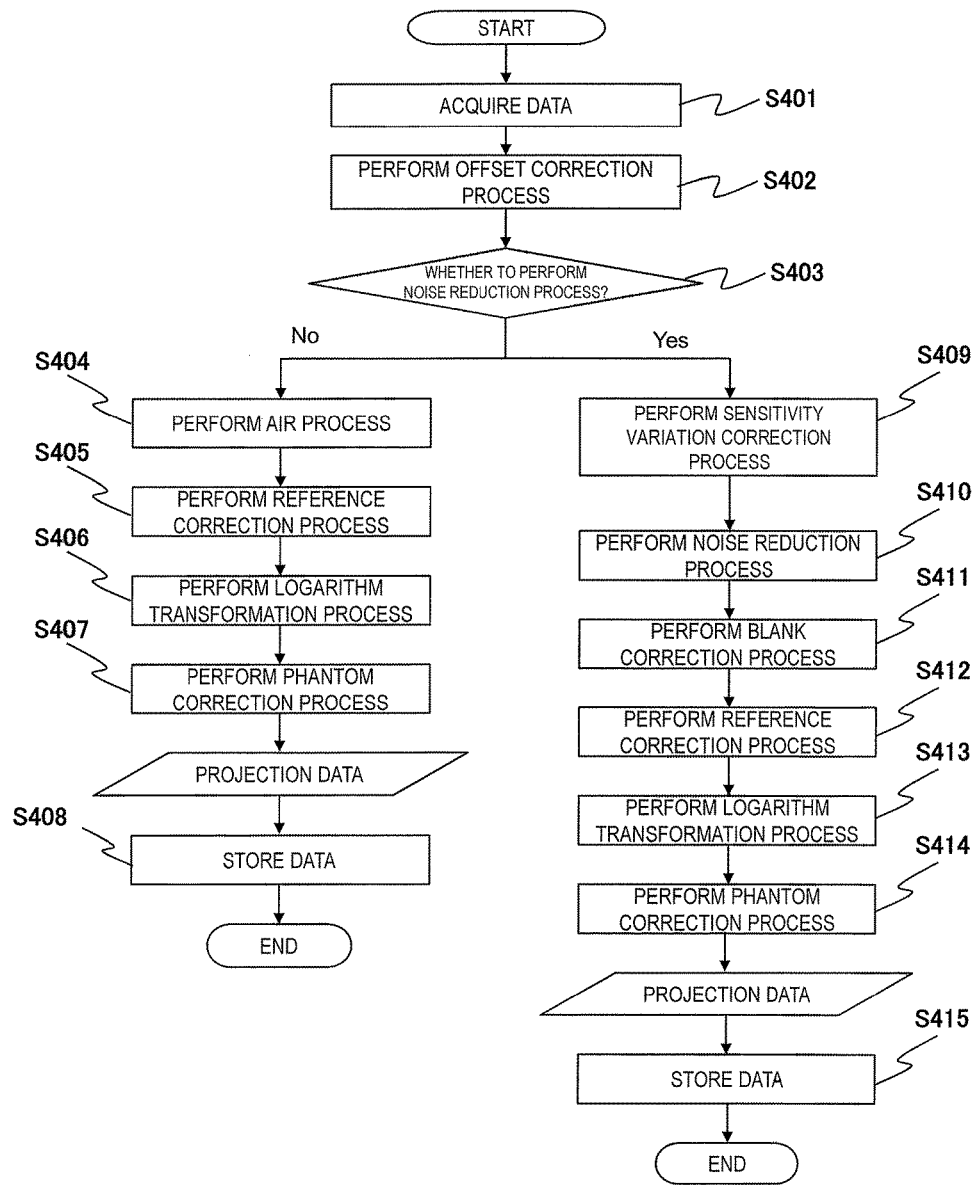
FIG. 11 is a flowchart illustrating a procedure in a projection data generation process according to a third embodiment.

FIG. 11 is a flowchart illustrating a process flow according to the third embodiment.

First, the image processing device 122 acquires the measurement data 50 obtained by scanning the object under a predetermined scanning condition (Step S401), and applies the offset correction process (Step S402). Thereafter, the selection whether or not to perform the noise reduction process on the measurement data is received (Step S403). In Step S403, the operator inputs an instruction indicating whether or not to perform the noise reduction process via the input device 121. The selection process in Step S403 may be performed prior to Step S401.

If an instruction indicating that the noise reduction process is not performed (Step S403; No), the process proceeds to Step S404. The processes in Step S404 to Step S408 are the same as those in the procedure of the projection data generation process in the related art. That is, the projection data is obtained by applying the air correction process using the air data 40 (Step S404), the reference correction process (Step S405), the logarithm transformation process (Step S406), and the phantom correction process (Step S407) to the measurement data 50 obtained after the offset correction process is performed in Step S402. The image processing device 122 causes the storage device 123 to store the prepared projection data (Step S408), and completes the projection data generation process.

On the other hand, in a case where an instruction indicating that the noise reduction process is performed is input in the selection process in Step S403 (Step S403; Yes), the process proceeds to Step S409. The processes in Step S409 to Step S415 are the same as those in the procedure of the projection data generation process (refer to FIG. 8) according to the first embodiment. That is, the sensitivity variation correction process is performed on the offset correction-processed measurement data (Step S409). The noise reduction process is performed on the sensitivity variation corrected measurement data 51 (Step S410). Thereafter, the blank correction process is applied (Step S411).

Thereafter, similarly to the processes in the related art, the image processing device 122 applies the reference correction process (Step S412), the logarithm transformation process (Step S413), and the phantom correction process (Step S414) to the object attenuation data obtained by the blank correction process, thereby obtaining the projection data 53. The image processing device 122 causes the storage device 123 to store the generated projection data 53 (Step S415), and completes a series of the projection data generation processes.

The processes in Step S409 to Step S415 may be substituted with the projection data generation process (Step S303 to Step S308 in FIG. 10) according to the second embodiment. In this case, the noise reduction process using the evaluation function in which the sensitivity variations are considered is performed.

As described above, the selection unit (input device 121) is further provided which receives selection whether or not to perform the noise reduction process from the measurement data. The projection data generation unit performs the noise reduction process in a case where it is selected to perform the noise reduction process via the input device 121.

In addition, the step of selecting whether or not to perform the noise reduction process from the measurement data is further provided. In the step of removing the sensitivity variation component and the noise, the noise reduction process is performed in a case where it is selected to perform the noise reduction process.

In this way, according to the third embodiment, a user's operation can select whether to improve image quality by applying the noise reduction process which needs a calculation time or whether to give priority to shortening the calculation time. Therefore, the third embodiment is practically adopted.

Hitherto, the preferred embodiments of the X-ray CT apparatus according to the present invention have been described. However, the present invention is not limited to the above-described embodiments. It will be apparent to those skilled in the art that various modification examples or correction examples are conceivable within the scope of the technical ideas disclosed in the present application. As a matter of course, it will be appreciated that the examples fall within the technical scope of the present invention.

REFERENCE SIGNS LIST

1 X-RAY CT APPARATUS,
100 SCAN GANTRY UNIT,
101 X-RAY SOURCE,
102 ROTARY DISC,
103 BOWTIE FILTER,
104 COLLIMATOR,
107 X-RAY DETECTOR,
120 OPERATION DESK,
121 INPUT DEVICE,
122 IMAGE PROCESSING DEVICE (DATA PROCESSING DEVICE),
123 STORAGE DEVICE,
124 SYSTEM CONTROL DEVICE,
125 DISPLAY DEVICE,
B1, B2 DETECTOR BLOCK,
C CLEARANCE,
31 SENSITIVITY VARIATION EXTRACTION UNIT,
32 PROJECTION DATA GENERATION UNIT,
40 AIR DATA,
41 SENSITIVITY VARIATION DATA,
42 BLANK DATA,
50 MEASUREMENT DATA,
51 SENSITIVITY VARIATION CORRECTION-PROCESSED MEASUREMENT DATA,
53 PROJECTION DATA

The invention claimed is:

1. An X-ray CT apparatus comprising:
a scan gantry unit that emits X-ray to an object, and that detects the X-ray transmitted through the object;
a bed on which the object is laid, and in which the object is loaded into or unloaded from an X-ray emission range of the scan gantry unit; and
an operation desk including a data processing device that controls each portion of the scan gantry unit, that acquires measurement data measured by the scan gantry unit, and that generates an image including an object tomographic image from the measurement data,
wherein the data processing device includes an extraction unit that acquires air data measured using the X-ray CT apparatus and the measurement data obtained by scanning the object, that extracts sensitivity variation data which is a sensitivity variation component of a detection element from the air data, and that extracts blank data from which the sensitivity variation component is removed, and a projection data generation unit that removes the sensitivity variation component and noise which are included in the measurement data, based on the sensitivity variation data, and that uses the blank data so as to perform a correction process of the measurement data from which the sensitivity variation component and the noise are removed.

2. The X-ray CT apparatus according to claim 1,
wherein based on the sensitivity variation data, after removing the sensitivity variation component included in the measurement data, the projection data generation unit performs an inter-proximity element smoothing process for removing the noise, and performs the correction process.

3. The X-ray CT apparatus according to claim 1,
wherein the projection data generation unit employs a successive approximation noise reduction method using an evaluation function including the sensitivity variation data so as to remove the sensitivity variation component and the noise from the measurement data, and performs the correction process.

4. The X-ray CT apparatus according to claim 1, further comprising:
an input device that receives selection whether or not to perform a noise reduction process from the measurement data,
wherein in a case where it is selected to perform the noise reduction process via the input device, the projection data generation unit performs the noise reduction process.

5. A data processing device comprising:
an extraction unit that acquires air data measured using an X-ray CT apparatus and measurement data obtained by scanning an object, that extracts sensitivity variation data which is a sensitivity variation component of a detection element from the air data, and that extracts blank data from which the sensitivity variation component is removed; and
a projection data generation unit that removes the sensitivity variation component and noise which are included in the measurement data, based on the sensitivity variation data, and that uses the blank data so as to perform a correction process of the measurement data from which the sensitivity variation component and the noise are removed.

6. The data processing device according to claim 5,
wherein based on the sensitivity variation data, after removing the sensitivity variation component included in the measurement data, the projection data generation unit performs an inter-proximity element smoothing process for removing the noise, and performs the correction process.

7. The data processing device according to claim 5,
wherein the projection data generation unit employs a successive approximation noise reduction method using an evaluation function including the sensitivity variation data so as to remove the sensitivity variation component and the noise from the measurement data, and performs the correction process.

8. The data processing device according to claim 5, further comprising:
an input device that receives selection whether or not to perform a noise, reduction process from the measurement data,
wherein in a case where it is selected to perform the noise reduction process via the input device, the projection data generation unit improves image quality, and in a case where it is selected not to perform the noise reduction process, the projection data generation unit gives priority to shortening a calculation time.

9. A projection data generation method comprising:
a step of causing a data processing device to acquire air data measured using an X-ray CT apparatus and measurement data obtained by scanning an object, to extract sensitivity variation data which is a sensitivity variation component of a detection element from the air data, and to extract blank data from which the sensitivity variation component is removed;
a step of removing the sensitivity variation component and noise which are included in the measurement data, based on the sensitivity variation data; and
a step of performing a correction process using the blank data on the measurement data from which the sensitivity variation component and the noise are removed.

10. The projection data generation method according to claim 9,
wherein in the step of performing the correction process, after the sensitivity variation component included in the measurement data is removed based on the sensitivity variation data, an inter-proximity element smoothing process for removing the noise is performed.

11. The projection data generation method according to claim 9,
wherein in the step of performing the correction process, a successive approximation noise reduction method using an evaluation function including the sensitivity variation data is employed so as to remove the sensitivity variation component and the noise from the measurement data.

12. The projection data generation method according to claim 9, further comprising:
a step of receiving selection whether or not to perform a noise reduction process from the measurement data,
wherein in the step of removing the sensitivity variation component and the noise, in a case where it is selected to perform the noise reduction process, the noise reduction process is performed.

* * * * *